US012669453B2

(12) United States Patent
Zhang et al.

(10) Patent No.: US 12,669,453 B2
(45) Date of Patent: Jun. 30, 2026

(54) METHOD FOR COAL ROCK RECOGNITION

(71) Applicants: Guizhou University, Guiyang City (CN); Guizhou Yihe Technology Co., Ltd., Guiyang (CN); Guizhou Yihe Mining Co., Ltd., Guiyang (CN)

(72) Inventors: Yiping Zhang, Guiyang City (CN); Genyi Long, Guiyang City (CN); Jie Zhang, Guiyang City (CN); Yunfeng Liu, Guiyang City (CN); Chengyu Jiang, Guiyang City (CN); Hao Chen, Guiyang City (CN); Hejiang Zhang, Guiyang City (CN); Yuyao Zhang, Guiyang City (CN)

(73) Assignees: Guizhou University, Guiyang (CN); Guizhou Yihe Technology Co., Ltd., Guiyang (CN); Guiihou Yihe Mining Co., Ltd., Guiyang (CN)

( * ) Notice: Subject to any disclaimer, the term of this patent is extended or adjusted under 35 U.S.C. 154(b) by 0 days.

(21) Appl. No.: 18/971,884

(22) Filed: Dec. 6, 2024

(65) Prior Publication Data

US 2026/0104372 A1     Apr. 16, 2026

(30) Foreign Application Priority Data

Oct. 15, 2024    (CN) .......................... 202411442997.6

(51) Int. Cl.
| | |
|---|---|
| *G01N 23/223* | (2006.01) |
| *E21B 44/00* | (2006.01) |
| *E21B 47/013* | (2012.01) |
| *E21B 47/017* | (2012.01) |
| *E21B 49/00* | (2006.01) |
| *G01N 33/24* | (2006.01) |

(52) U.S. Cl.
CPC ........... *G01N 23/223* (2013.01); *E21B 44/00* (2013.01); *E21B 47/013* (2020.05);
(Continued)

(58) Field of Classification Search
CPC ................. G01N 23/223; G01N 33/24; G01N 2223/616; E21B 44/00; E21B 47/013; E21B 47/017; E21B 49/00
See application file for complete search history.

(56) References Cited

U.S. PATENT DOCUMENTS

| | | | | |
|---|---|---|---|---|
| 3,448,264 A | * | 6/1969 | Rhodes ................ | G01N 23/223 |
| | | | | 378/46 |
| 5,272,745 A | * | 12/1993 | Smallbone ........... | G01N 23/223 |
| | | | | 378/45 |

(Continued)

FOREIGN PATENT DOCUMENTS

| | | | | |
|---|---|---|---|---|
| CN | 105190364 A | * | 12/2015 | ............. G01V 5/104 |

OTHER PUBLICATIONS

Ellison, C., Abdelsayed, V., Smith, M. and Shekhawat, D., 2022. Comparative evaluation of microwave and conventional gasification of different coal types: Experimental reaction studies. Fuel, 321, p. 124055. DOI: https://doi.org/10.1016/j.fuel.2022.124055 (Year: 2022).*

(Continued)

*Primary Examiner* — Theodore N Yao
(74) *Attorney, Agent, or Firm* — Birchwood IP

(57) ABSTRACT

A device for coal rock recognition while drilling is disclosed. The device includes an elemental analyzer arranged on a drill pipe. A coal rock recognition information monitoring panel is connected to the elemental analyzer by a data cable. A circuit board is arranged in the elemental analyzer and a processor mounted on the circuit board. A detection head is connected to the circuit board and arranged on a side wall of the elemental analyzer. The detection head includes a detector and an X-ray tube.

7 Claims, 1 Drawing Sheet

(52) U.S. Cl.
CPC ............ *E21B 47/017* (2020.05); *E21B 49/00*
(2013.01); *G01N 33/24* (2013.01); *G01N*
*2223/616* (2013.01)

(56) References Cited

U.S. PATENT DOCUMENTS

| | | | | |
|---|---|---|---|---|
| 2013/0066605 A1* | 3/2013 | Li | ......................... | G01N 23/223 |
| | | | | 703/2 |
| 2018/0238148 A1* | 8/2018 | Canady | ................ | G01V 11/002 |
| 2021/0372260 A1* | 12/2021 | Poulson | .................. | E21B 44/02 |

OTHER PUBLICATIONS

Ellison, C., Abdelsayed, V. and Smith, M.W., 2023. Analysis of char structure and composition from microwave and conventional pyrolysis/ gasification of low and middle rank coals. Fuel, 354, p. 129301. DOI: https://doi.org/10.1016/j.fuel.2023.129301 (Year: 2023).*

Abdelsayed, V., Ellison, C.R., Trubetskaya, A., Smith, M.W. and Shekhawat, D., 2019. Effect of microwave and thermal co-pyrolysis of low-rank coal and pine wood on product distributions and char structure. Energy & fuels, 33(8), pp. 7069-7082. DOI: https://doi.org/10.1021/acs.energyfuels.9b01105 (Year: 2019).*

Ellison, C., Mullen, C.A. and Elkasabi, Y., 2026. Analytical and experimental study of switchgrass and agricultural plastic co-pyrolysis in a microwave reactor. Fuel, 406, p. 136771. DOI: https://doi.org/10.1016/j.fuel.2025.136771 (Year: 2026).*

Candice Ellison,et al (2018) Dielectric characterization of bentonite clay at various moisture contents and with mixtures of biomass in the microwave spectrum, Journal of Microwave Power and Electromagnetic Energy, 52:1, 3-15, DOI: 10.1080/08327823.2017. 1421407 (Year: 2018).*

* cited by examiner

METHOD FOR COAL ROCK RECOGNITION

CROSS-REFERENCE TO RELATED APPLICATION

This patent application claims the benefit and priority of Chinese Patent Application No. 2024114429976, filed with the China National Intellectual Property Administration on Oct. 15, 2024, the disclosure of which is incorporated by reference herein in its entirety as part of the present application.

TECHNICAL FIELD

The present disclosure relates to the technical field of coal rock recognition, and in particular to a device for coal rock recognition while drilling based on an elemental analyzer.

BACKGROUND

Coal rock recognition technology is widely used in coal mining and tunneling equipment in the field of coal resource exploitation, which can automatically adjust parameters such as height and direction of coal cutting and tunneling, thus avoiding excessive mining of rocks. However, in the field of gas prevention and control, there are few coal rock recognition technologies for fracturing pressure relief of coal seam by drilling. At present, the coal seam and rock during drilling are mainly recognized by human judgment of workers or simple physical detection means, which is prone to misjudgment and less in information acquisition.

In recent years, with the development of coal rock recognition technology, scholars in China and at abroad have gradually deepened their research on elemental analyzers such as spectral analysis, X-ray fluorescence and neutron activation analysis, and it is increasingly urgent to apply the elemental analyzer to the drill pipe for coal rock recognition.

In the process of pressure relief by boreholes, when the drill pipe is used for operation, it is crucial to accurately recognize the coal seam and rock near the drill bit to construct a transparent geological guarantee system that matches the intelligent coal mine construction. The device for coal rock recognition while drilling based on element analyzer can well perform coal rock recognition while drilling, and has the advantages of synchronous monitoring while drilling, intuitive data display, etc. The information of composition of the coal rock in the borehole can be acquired specifically in real time, and the purpose of transparency of geological conditions is satisfied.

SUMMARY

An objective of the present disclosure is to provide a device for coal rock recognition while drilling based on an elemental analyzer, which is used for synchronous detection, exploration while drilling, rapid recognition and specific display, and for geological information exposure and exploration, thus achieving accurate recognition of geological conditions and improving the accuracy of drilling. Secondly, the device is connected to a drill pipe for monitoring synchronously while drilling, thus improving the efficiency of exploration.

To achieve the objective above, the present disclosure employs the following technical solution:

The present disclosure provides a device for coal rock recognition while drilling based on an elemental analyzer, including an elemental analyzer arranged on a drill pipe, and a coal rock recognition information monitoring panel connected to the elemental analyzer through a data cable.

A circuit board and a processor are arranged in the elemental analyzer, and a detection head connected to the circuit board is arranged on a side wall of the elemental analyzer. The detection head includes a detector, and an X-ray tube.

Further, a lower end part of the drill pipe is provided with a drill bit, the elemental analyzer is a cylindrical structure for connecting the drill pipe and the drill bit, and a rotating outer diameter of the elemental analyzer is less than that of the drill bit.

Further, the drill pipe is a directional cable drill pipe, and an orifice channel for laying the data cable is formed in the drill pipe. The data cable includes a data transmission line, and a current delivery line, thus supplying power and transmit a signal to the elemental analyzer.

Further, the side wall of the elemental analyzer is provided with a reserved groove for installing the detector and the X-ray tube, and a wear-resistant protective film is arranged outside the reserved groove.

The detector is connected to the circuit board, a processor is connected to the circuit board, and detection data collected by the processor is derived to the coal rock recognition information monitoring panel through the data cable.

The coal rock recognition information monitoring panel includes a host, and a display.

Further, an end face of the elemental analyzer is provided with a line hole for connecting the data cable.

The present disclosure provides a method for coal rock recognition while drilling based on elemental analyzer, including the following steps:

installing a coal rock recognition monitoring panel on a drilling well, and connecting the coal rock recognition information monitoring panel to a drill pipe through a data cable;

driving, by a motor, the drill pipe to drill and punch a hole, after drilling for a certain distance, controlling a drill bit to stop drilling, and starting an elemental analyzer for coal rock recognition and detection; then starting the motor to drive the drill pipe to rotate by 180°, thus driving the elemental analyzer to rotate; afterwards, irradiating X-rays to a wall of a borehole using an X-ray tube, thus exciting carbon, silicon and unknown elements in coal rock to be detected to generate secondary X-ray reflection; collecting energy and wavelength of the emitted secondary X-rays by a detector and transmitting the collected energy and wavelength to a circuit board and a processor, and comparing corresponding elements one by one through the corresponding energy and wavelength to determine elements with corresponding energy and wavelength; detecting again and transmitting data to the coal rock recognition information monitoring panel through the data cable, and displaying and recording drilling data on the panel in real time; after completing a set of tests, continuing to drill for a certain distance and carrying out coal rock recognition, and repeating the step repeatedly until the drilling is finished.

Compared with the prior art, the present disclosure has beneficial effects as follows: The elemental analyzer is combined and applied to coal rock recognition in a borehole, and is integrally connected to a directional cable drill pipe to achieve an effect of entering while drilling and real-time monitoring. Such a design can achieve coal rock recognition by synchronizing the drilling process, the detection can be carried out without drilling withdrawal, and thus the detection efficiency is improved. The elemental analyzer can rapidly recognize the elements of a substance, thus providing accurate and real-time information for the worker. The detection head is wrapped with a wear-resistant protective film, which can protect a detector and an X-ray tube, and is convenient for replacement. Meanwhile, the coal rock recognition information monitoring panel can analyze the data in real time and display the composition of coal rock in a borehole intuitively and clearly, which effectively solves the shortcomings of human misjudgment or inaccurate physical and mechanical monitoring. The transparency of geological information is effectively increased through data recording and analysis.

BRIEF DESCRIPTION OF THE DRAWINGS

The present disclosure is further described below with reference to accompanying drawings.

Figure 1:
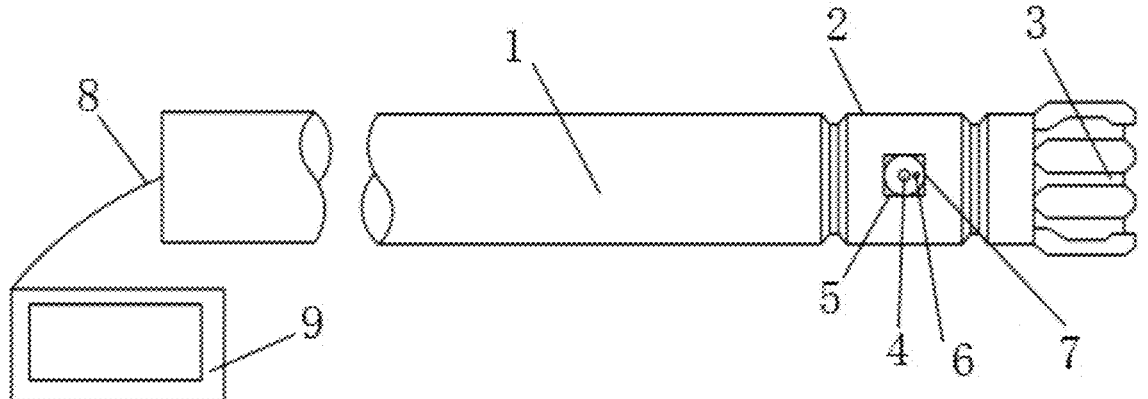
FIG. 1 is a schematic diagram of a main body of a device for coal rock recognition while drilling based on an elemental analyzer according to the present disclosure.

In the drawings: 1—drill pipe; 2—elemental analyzer; 3—drill bit; 4—detector; 5—wear-resistant protective film; 6—X-ray tube; 7—detection head; 8—data cable; 9—coal rock recognition information monitoring panel; 10—circuit board.

DETAILED DESCRIPTION OF THE EMBODIMENTS

Figure 2:
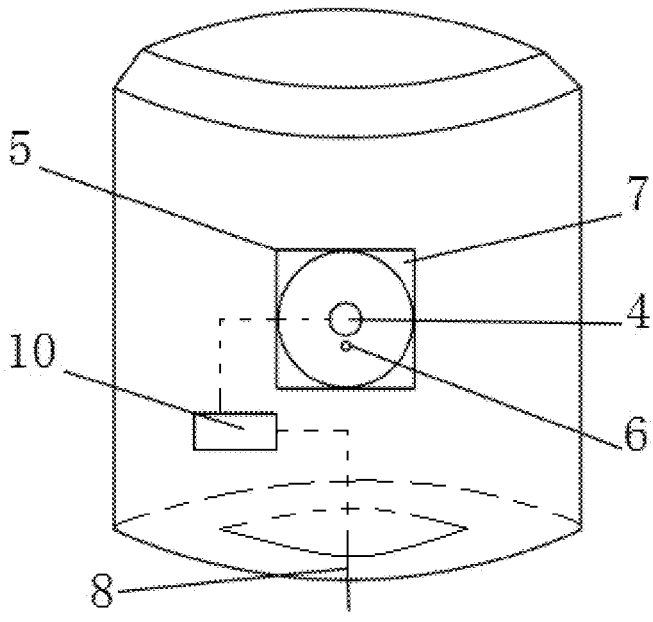
FIG. 2 is a schematic structural diagram of an elemental analyzer in a device for coal rock recognition while drilling based on an elemental analyzer according to the present disclosure.

As shown in FIG. 1 and FIG. 2, the present disclosure provides a device for coal rock recognition while drilling based on an elemental analyzer, including an elemental analyzer 2 arranged on a drill pipe 1, and a coal rock recognition information monitoring panel 9 connected to the elemental analyzer 2 through a data cable 8. A circuit board 10 and a processor are arranged in the elemental analyzer 2, and a detection head 7 connected to the circuit board is arranged on a side wall of the elemental analyzer 2. The detection head 7 includes a detector 4, and an X-ray tube 6.

In this embodiment, a lower end part of the drill pipe 1 is provided with a drill bit 3. During use, the drill bit 3 is installed at a lower end of the drill pipe 1, and a rotary mechanism and a transmission motor are installed on an upper end of the drill pipe.

During specific implementation, as shown in FIG. 2, the elemental analyzer 2 is a cylindrical structure for connecting the drill pipe 1 and the drill bit 3, and a rotating outer diameter of the elemental analyzer 2 is less than that of the drill bit 3. Specifically, a radius of the elemental analyzer 2 is close to that of the drill pipe 1, thus ensuring that the elemental analyzer 2 cannot damage a borehole and fit the borehole.

In this embodiment, the drill pipe 1 is a directional cable drill pipe, an orifice channel for laying the data cable 8 is formed in the drill pipe 1. The data cable 8 includes a data transmission line, and a current delivery line, thus supplying power and transmit a signal to the elemental analyzer 2. The data cable 8 has a function of data transmission and current delivery.

In this embodiment, the side wall of the elemental analyzer 2 is provided with a reserved groove for installing the detector 4 and the X-ray tube 6. A wear-resistant protective film 5 is installed outside the reserved groove. The detection head 7 is closely protected with the wear-resistant protective film 5, specifically, the detection head 7 is in smooth transition with an outer wall of the elemental analyzer 2, thus ensuring that the detection head 7 cannot be worn during drilling. Moreover, the wear-resistant protective film 5 can be replaced according to the degree of wear, specifically, the wear-resistant protective film can be by a fastener. The wear-resistant protective film 5 is made of a wear-resistant and ash-free material (such as glass or tempered glass), thus ensuring the detection accuracy of the detection head 7.

In this embodiment, the detector 4 is connected to the circuit board 10, a processor is connected to the circuit board 10, and detection data collected by the processor is derived to the coal rock recognition information monitoring panel 9 through the data cable 8. The coal rock recognition information monitoring panel 9 includes a host, and a display, which can be used to perform element analysis on the data input through the data cable, thus performing coal rock recognition on a substance near the detection head, and displaying the information on the display.

In this embodiment, an end face of the elemental analyzer 2 is provided with a line hole for connecting the data cable 8 for line arrangement.

The present disclosure provides a method for coal rock recognition while drilling based on an elemental analyzer, including the following steps:

A coal rock recognition monitoring panel 9 is installed on a drilling well, and is connected to a drill pipe 1 through a data cable 8. The worker can get the composition of the coal seam or rock near the drill bit 3 through the coal rock recognition information monitoring panel 9. If the detector continuously monitors the rock, it can be determined that the drill bit is drilling into the rock stratum, and the drilling can be stopped.

The drill pipe 1 is driven by the motor to drill and punch a hole. After drilling for a certain distance, a drill bit 3 is controlled to stop drilling, and an elemental analyzer 2 is started for coal rock recognition and detection. Then, the motor is started to drive the drill pipe to rotate by 180°, thus driving the elemental analyzer 2 to rotate. Afterwards, X-rays are irradiated to a wall of a borehole by using an X-ray tube, thus exciting carbon, silicon, and unknown elements in the coal rock to be detected to generate secondary X-ray reflection. Energy and wavelength of the emitted secondary X-rays are collected by a detector 4 and transmitted to a circuit board 10 and a processor, and corresponding elements are compared one by one through the corresponding energy and wavelength to determine elements with corresponding energy and wavelength. The detection is carried out once again (repeating the step above), and the data is transmitted to the coal rock recognition information monitoring panel 9 through the data cable 8, and drilling data is displayed in real time and recorded on the panel. After a set of tests is completed, the drill bit continues to drill for a certain distance for coal rock recognition, and the step is repeatedly repeated until the drilling is finished.

The above embodiments are only the description of the preferred embodiments created by the present disclosure, and are not intended to limit the scope of the present disclosure. Various variations and improvements made by those of ordinary skill in the art to the technical solution of the present disclosure without departing from the design spirit of the present disclosure shall fall within the scope of protection determined by the claims of the present disclosure.

What is claimed is:

1. A method for coal rock recognition while drilling based on an elemental analyzer, the method comprising:

installing a coal rock recognition information monitoring panel on a drilling well;

connecting the coal rock recognition information monitoring panel to a drill pipe through a data cable;

driving, by a motor, the drill pipe to drill and punch a hole;

after drilling for a certain distance, controlling a drill bit to stop drilling and starting the elemental analyzer for coal rock recognition and detection;

then starting the motor to drive the drill pipe to rotate by 180° to drive the elemental analyzer to rotate;

afterwards, irradiating X-rays to a wall of a borehole using an X-ray tube thereby exciting carbon, silicon and unknown elements in coal rock to be detected to generate secondary X-ray reflection;

collecting energy and wavelength of emitted secondary X-rays by a detector;

transmitting the collected energy and wavelength to a processor;

comparing corresponding elements one by one through corresponding energy and wavelength to determine elements with corresponding energy and wavelength;

detecting again and transmitting data to the coal rock recognition information monitoring panel through the data cable; and displaying and recording drilling data on the panel in real time.

2. The method according to claim 1, further comprising, after completing a set of tests, continuing to drill for a certain distance and carrying out the coal rock recognition.

3. The method according to claim 1, wherein the method is repeatedly performed until the drilling is finished.

4. The method according to claim 1, wherein a lower end part of the drill pipe is provided with the drill bit, the elemental analyzer is a cylindrical structure for connecting the drill pipe and the drill bit, and a rotating outer diameter of the elemental analyzer is less than that of the drill bit.

5. The method according to claim 4, wherein:

the drill pipe is a directional cable drill pipe;

an orifice channel for laying the data cable is formed in the drill pipe; and the data cable comprises a data transmission line and a current delivery line configured to supply power and transmit a signal to the elemental analyzer.

6. The method according to claim 5, wherein:

a side wall of the elemental analyzer is provided with a reserved groove for installing the detector and the X-ray tube;

a wear-resistant protective film is arranged outside the reserved groove;

the detector and the processor are connected to a circuit board;

detection data collected by the processor is provided to the coal rock recognition information monitoring panel through the data cable; and the coal rock recognition information monitoring panel comprises a host and a display.

7. The method according to claim 6, wherein an end face of the elemental analyzer is provided with a line hole for connecting the data cable.

* * * * *